United States Patent [19]

McCool et al.

[11] Patent Number: 5,674,234
[45] Date of Patent: Oct. 7, 1997

[54] FLEXIBLE SURGICAL RAZOR

[75] Inventors: Gregory F. McCool, Staunton; Jeffrey W. Wonderley, Fort Defiance, both of Va.; Robert J. Segal, Quincy, Ill.

[73] Assignee: American Safety Razor Company, Verona, Va.

[21] Appl. No.: 373,938

[22] Filed: Jan. 13, 1995

Related U.S. Application Data

[63] Continuation-in-part of Ser. No. 313,597, Sep. 29, 1994.
[51] Int. Cl.$^6$ .................................................. A61B 7/32
[52] U.S. Cl. ........................ 606/167; 30/32; 30/346.5
[58] Field of Search .................................. 606/131, 132, 606/167; 30/32, 47, 48, 49, 50, 353, 346.5, 346.55, 346.61

[56] References Cited

U.S. PATENT DOCUMENTS

| | | | |
|---|---|---|---|
| 951,456 | 3/1910 | Saxton | 30/49 |
| 1,174,932 | 3/1916 | Grenier. | |
| 1,893,524 | 1/1933 | Shanley | 606/161 |
| 1,934,151 | 11/1933 | Slama et al.. | |
| 1,974,568 | 9/1934 | Grotenhuis | 30/34.05 |
| 2,035,110 | 3/1936 | Becker et al.. | |
| 2,041,778 | 5/1936 | Peters. | |
| 2,361,921 | 11/1944 | Albert. | |
| 2,453,198 | 11/1948 | Corbett | 30/312 |
| 3,583,403 | 6/1971 | Pohl et al. | 606/132 |
| 3,688,407 | 9/1972 | Paquette. | |
| 3,916,418 | 10/1975 | Neveu. | |
| 4,038,986 | 8/1977 | Mahler. | |
| 4,221,222 | 9/1980 | Detsch. | |
| 4,438,767 | 3/1984 | Nelson. | |
| 4,516,320 | 5/1985 | Peleckis | 30/49 |
| 4,651,734 | 3/1987 | Doss et al.. | |
| 4,690,139 | 9/1987 | Rosenberg. | |
| 4,782,590 | 11/1988 | Pope | 30/50 |
| 4,887,356 | 12/1989 | Rudd, Sr.. | |
| 4,893,641 | 1/1990 | Strickland. | |
| 4,943,295 | 7/1990 | Hartlaub et al. | 606/131 |

OTHER PUBLICATIONS

American V. Mueller The Surgical Armamentarium p. 103 (1980).
DermQuest—"Introducing A Revolutionary New Biopsy Shaver" Brochure, Tampa, Florida (Jul. 1994).

Primary Examiner—Michael Powell Buiz
Assistant Examiner—Patrick W. Rasche
Attorney, Agent, or Firm—McDermott, Will & Emery

[57] ABSTRACT

A flexible surgical razor for removing organic tissue, such as lesions, moles, corns and the like, at or below the skin's surface. The surgical razor utilizes a flexible blade with a well-honed front edge and left and right gripping extensions formed attached to the left and right side edges of the blade, respectively. Each gripping extension includes an inner segment extending in the same plane as the blade, a middle segment extending at an upward angle away from the plane of the blade, and an exterior segment, with exterior gripping edges, extending at an intersecting angle with the middle segment. The gripping edges include a plurality of teeth in rows asymmetrically angled to the plane of the flexible blade for full and complete control of blade flexing. A flexible sheath is added to regulate the shape and extent of the blade's curvature. The user applies inward finger pressure to both gripping extensions simultaneously which bends the flexible blade in a curved fashion.

23 Claims, 9 Drawing Sheets

FLEXIBLE SURGICAL RAZOR

This is a continuation-in-part application U.S. Ser. No. 08/313,597 filed on Sep. 29, 1994.

BACKGROUND OF THE INVENTION

The present invention is directed to an improved surgical instrument for cutting organic tissue at or below the skin's surface by employing a flexible blade with specially designed gripping extensions at both ends.

Medical professionals often remove organic tissue, such as lesions, moles, corns and the like, from the surface of a patients skin. Surgeons typically utilize a scalpel for such procedures, cutting around the appropriate area and to the desired depth. Removal of the organic tissue, however, also requires cutting underneath the unwanted tissue, and the scalpel is an awkward an inefficient tool for making such incisions. The straight and rigid scalpel blade requires angular cuts toward the center of the tissue to be removed, which results in the removal of more tissue than necessary. Consequently, many medical professionals have sought more efficient methods for performing such procedures.

Doctors utilize various instruments for cutting thin organic tissue sections for transplanting or grafting, such as U.S. Pat. Nos. 4,038,986 and 3,583,403. These instruments, however, are not designed for the removal of skin protuberances extending from below the skins surface. Such grafting devices shave large thin tissue sections of a preset width and thickness, and achieve smooth continuous cuts. Removal of small sections corresponding to lesions, moles, corns and the like ideally requires a thin flexible and readily adjustable blade for cutting small sections at varying depths.

One particular flexible surgical cutting tool, U.S. Pat. No. 4,943,295, is designed for the removal of skin protuberances, and utilizes a thin flexible blade with finger grips and a sheath covering the rear margin of the blade. The surgeon applies pressure to the finger grips and bends the device to a desired degree of curvature depending on the width and depth of the intended incision. This invention, however, lacks a finger grip design for regulating the blade's flex. Moreover, this invention lacks a sheath design for controlling the shape and extent of the blade's curvature during use.

The present invention combines a flexible blade with gripping extensions designed to regulate the direction of the blade's flex and improve the surgeon's control over the extent of the blade's flex. Furthermore, the present invention teaches a method of varying the flexible sheath design for control over the shape and extent of the flexible blade's curvature.

SUMMARY OF THE INVENTION

The present invention provides a razor for removal of organic tissue, such as lesions, moles, corns and the like, at or below the skin's surface. The razor incorporates a flexible blade and a pair of gripping extensions. The flexible blade includes a well-honed front edge, a left side edge, a right side edge, a front edge, and a rear edge. The pair of gripping extensions are attached to the side edges of the flexible blade. The flexible blade may be bent to an appropriate curved cutting shape through the application of inward finger pressure on both gripping extensions simultaneously, while grasping the razor between the finger-tips.

Each gripping extension includes an inner, a middle and an outer segment. The inner segment is attached to a blade side edge and extends outward from the blade. The middle segment extends at an upward angle away from the plane of the blade. The outer sediment has an exterior gripping edge and extends at an intersecting angle with the middle segment. Each gripping edge includes a row of a plurality of teeth to provide suitable gripping surfaces by fingers and appropriate pressure. The points where the finger pressure is applied are thus above the plane of the flexible blade, a configuration which regulates the direction of the flexible blade's curvature and enhances the user's ability to control the extent of that curvature.

In another embodiment, the invention comprises a flexible blade having a keen front edge, left and right side edges, and a rear edge. A pair of gripping extensions each has an inner segment attached to a side edge of the said blade, a middle segment extending at an upward angle away from the plane of the blade, and an outer segment having an exterior gripping edge and extending at an intersecting angle with said middle segment. The gripping edge includes a first and second row of plurality of spaced apart teeth for finger engagement, the first and second rows of the spaced apart teeth asymmetrically angled to the middle segment. The flexible blade flexes upon application of pressure by finger engagement of the gripping extension, with the fingers engaging the second row of teeth as the blade is flexed.

The invention may further include a flexible sheath that runs along the top surface of the flexible blade, and is attached to the gripping extensions. The front and rear edges of the flexible sheath are set inward from the front and rear edges of the flexible blade, respectively. Furthermore, the thickness, width and shape of the sheath controls the flexibility of the razor. This flexibility regulates the user's control over the extent and shape of the flexible blade's curvature.

As pointed out in greater detail below, the razor of this invention provides important improvements and advantages over the existing art. The design of the gripping extensions facilitates efficient control over the direction and extent of the flexible blade's curvature during use. The row or rows of flexible teeth ensure that as the blade is flexed, the user's fingers have an full and complete control of the flexing blade. The design of the flexible sheath further enhances this control and also regulates the shape of the flexible blade's curvature. These advantages and improvements provide for a more versatile and effective razor.

The invention itself, taken together with further objects and attendant advantages, will best be understood by reference to the following detailed description taken in conjunction with the accompanying drawings.

DETAILED DESCRIPTION

Figure 2:
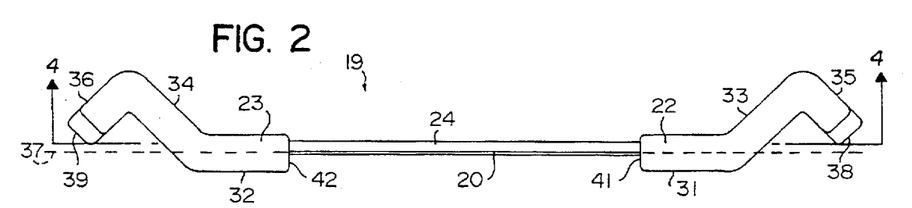
FIG. 2 is a front view of the flexible surgical razor of FIG. 1.
Figure 3:
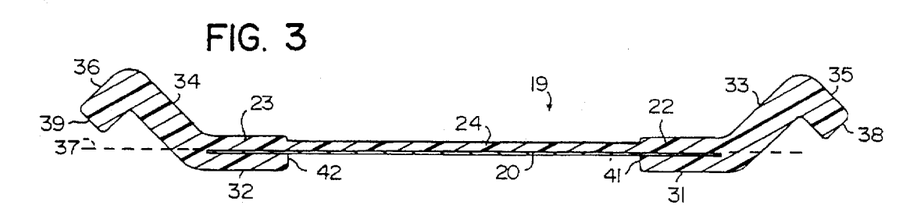
FIG. 3 is a cross section taken along line A-A' of FIG. 1.
Figure 4:
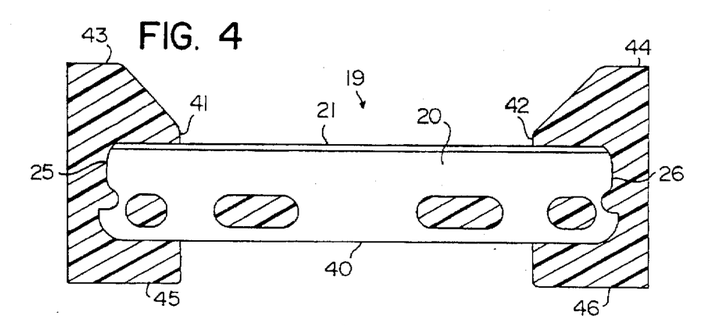
FIG. 4 is a cross section taken along line B-B' of FIG. 2.

Turning to the drawings and a first embodiment of the invention, FIGS. 1–5 show a flexible surgical razor 19 for cutting organic skin tissue, such as lesions, moles, corns and the like, at or below the skin's surface. The flexible surgical razor 19 utilizes a thin, flexible blade 20 with a well-honed front edge 21, left and right gripping extensions 22 and 23, respectively, and a flexible sheath 24. As shown in FIG. 4, the flexible blade also includes left and right side edges 25 and 26, respectively.

FIGS. 2 and 3 illustrate the configuration of the left and right gripping extensions 22 and 23. The left and right inner segments 31 and 32 are attached to the flexible blade's left and right side edges 25 and 26, respectively, and extend outward from the flexible blade 20 with the left and right interior edges 41 and 42 facing inward towards the flexible blade 20. The right and left middle segments 33 and 34 extend outward from the left and right inner segments 31 and 32, respectively, and at upward angles away from the plane of the blade 37. The left and right outer segments 35 and 36, have exterior edges 38 and 39 for gripping, and extend outward from the middle segments 33 and 34, respectively, at intersecting angles with the left and right middle segments 33 and 34. The left and right front edges 43 and 44 of the left and right gripping extensions 22 and 23, respectively, run parallel to the front edge 21 of the flexible blade 20, and the left and right rear edges 45 and 46 of the left and right gripping extensions 22 and 23, respectively, run parallel to the rear edge 40 of the flexible blade 20.

The points where the inward finger pressure is applied to the left and right exterior edges 38 and 39 of the left and right gripping extensions 22 and 23 are thus above the plane of the blade 37. This configuration regulates the direction of the blade's curvature because the inward forces act above the plane of the blade 37 and thus create a resultant downward force on the flexible blade 20. Moreover, the gripping extension design enhances the user's ability to control the extent of the flexible blade's curvature through more efficient translation of the forces applied by the finger pressure.

Figure 1:
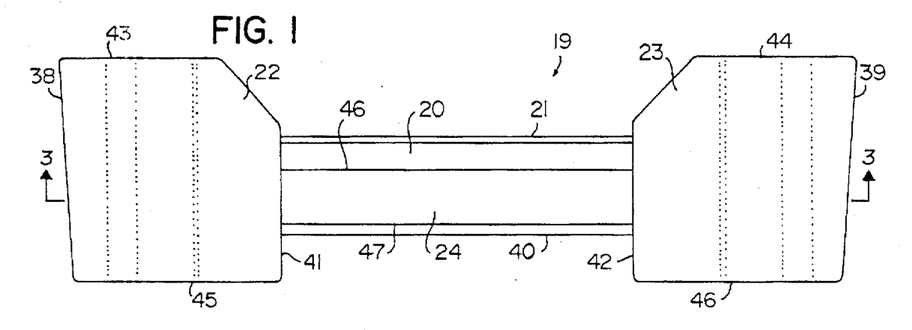
FIG. 1 is a top view of the flexible surgical razor of a first embodiment of this invention.

The flexible sheath 24 runs across the top surface of the flexible blade 20, and attaches to the left and right interior edges 41 and 42 of the left and right gripping extensions 22 and 23, as depicted in FIGS. 1, 2 and 3. The front and rear edges 46 and 47 of the flexible sheath 24 are set inward from the front and rear edges 21 and 40 of the flexible blade 20, respectively. The thickness, width and shape of the flexible sheath 24 control the flexibility of the flexible surgical razor 19. Decreases in the thickness and/or width of the flexible sheath 24 will result in greater blade flexibility at the corresponding blade areas. The flexible blade's degree of curvature, therefore, will increase at the areas where the flexible sheath's thickness and/or width decreases.

Figure 5:
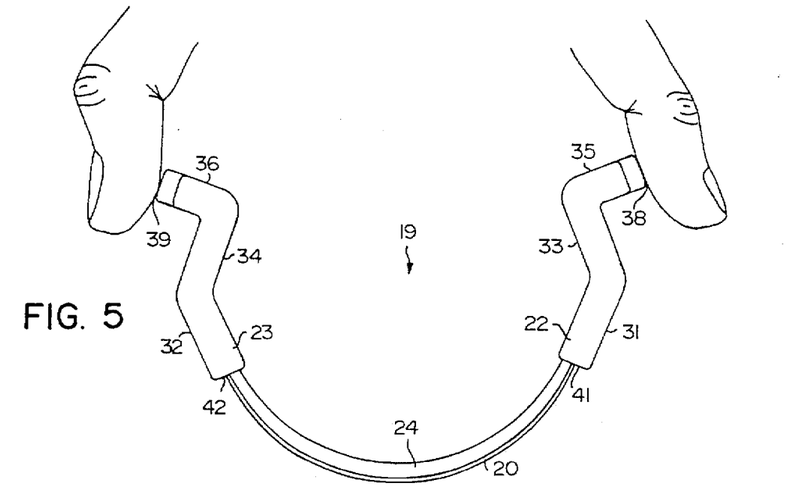
FIG. 5 is a front view of the flexible surgical razor of FIG. 1 in its flexed position as employed for the removal of organic skin tissue.

The flexibility of this surgical razor enables the user to flex the instrument to an appropriate degree of curvature depending on the size and depth of the desired cut. The user curves the flexible blade 20 by applying inward pressure on the left and right exterior edges 38 and 39 of the left and right gripping extensions 22 and 23 simultaneously, while grasping the instrument between the finger-tips, as depicted in FIG. 5. The user controls the degree of curvature through the magnitude of the applied pressure. The flexible sheath 24 regulates the degree and shape of the flexible blade's curvature in accordance with the sheath's flexibility. Accordingly, the sheath's flexibility regulates the user's control over the extent and shape of the blade's curvature, as exhibited by the third and fourth embodiments described below.

Figure 6:
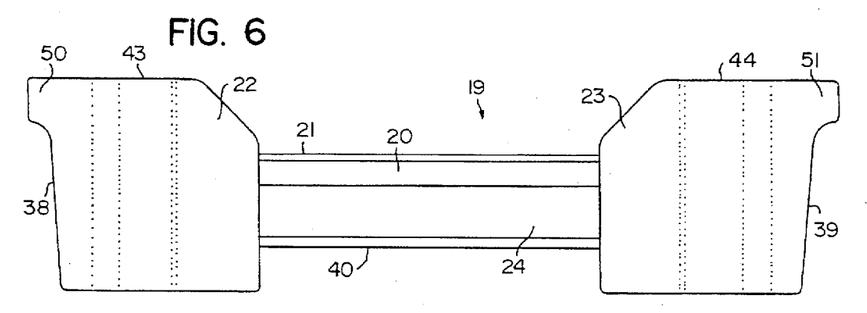
FIG. 6 is a top view of the flexible surgical razor of a second embodiment of this invention.
Figure 7:
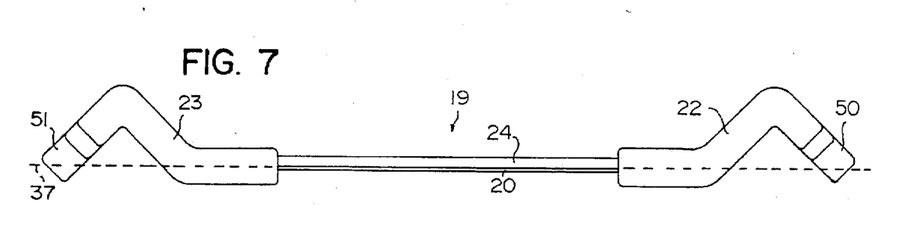
FIG. 7 is a front view of the flexible surgical razor of FIG. 6.

FIGS. 6 and 7 illustrate a second embodiment of the flexible surgical razor 19. This embodiment is identical to the first embodiment, described above, except for the addition of left and right protruding tabs 50 and 51, extending from the left and right exterior edges 38 and 39 of the left and right gripping extensions 22 and 23, respectively. The left and right protruding tabs 50 and 51 run along the left and right front edges 43 and 44 of the left and right gripping extensions 25 and 23, respectively. The left and right protruding tabs 50 and 51 provide surfaces for the user to press their finger tips against while guiding the flexible blade across the surface of the patient's skin.

Figure 8:
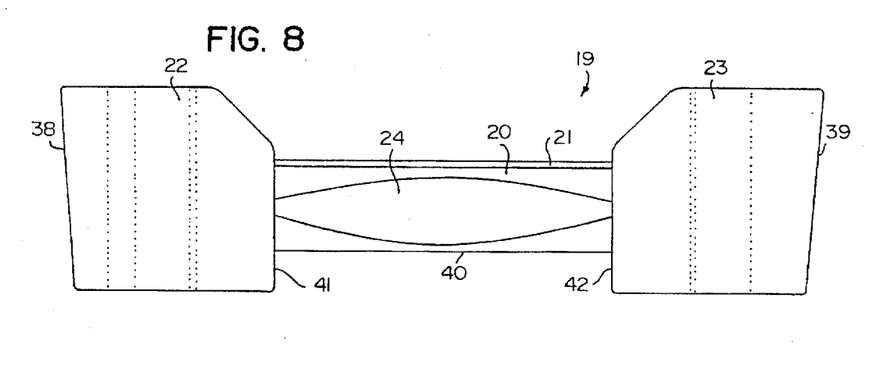
FIG. 8 is a top view of the flexible surgical razor of a third embodiment of this invention.
Figure 9:
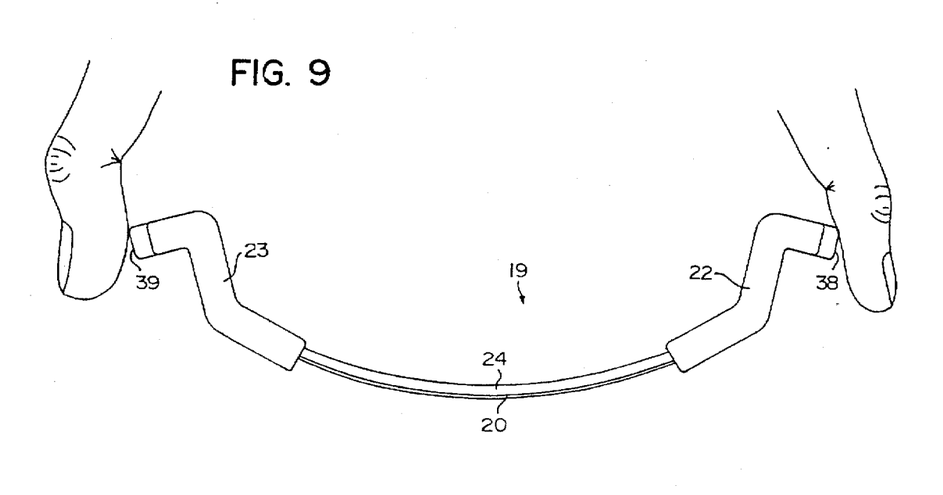
FIG. 9 is a front view of the flexible surgical razor of FIG. 8 in its flexed position as employed for the removal of organic skin tissue.
Figure 10:
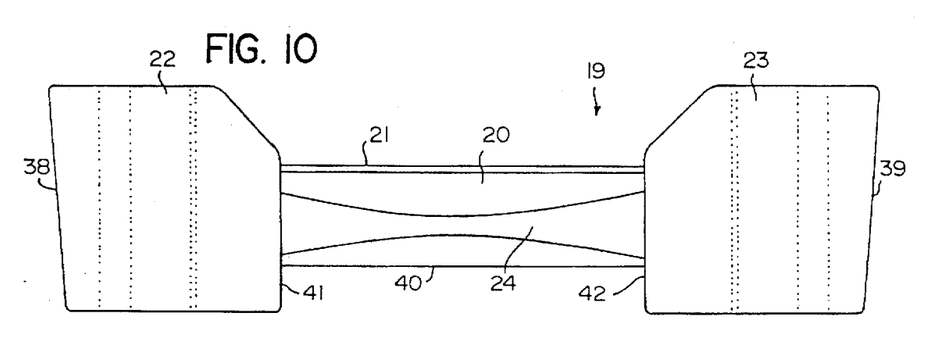
FIG. 10 is a top view of the flexible surgical razor of a fourth embodiment of the present invention.

A third embodiment of the flexible surgical razor 19, in FIGS. 9 and 10, illustrates a modified flexible sheath design. This embodiment is identical to the first embodiment, described above, except that the front and rear edges 46 and 47 of the flexible sheath 24 are designed with a convex shape, as illustrated in FIG. 8. This flexible sheath design will result in a flex as depicted in FIG. 9. The wider portion of the flexible sheath 24 will react less to inward finger pressure applied to the left and right exterior edges 38 and 39 of the left and right gripping extensions 22 and 23 than the narrower portions. This produces the lesser degree of curvature portrayed in FIG. 9.

Figure 11:
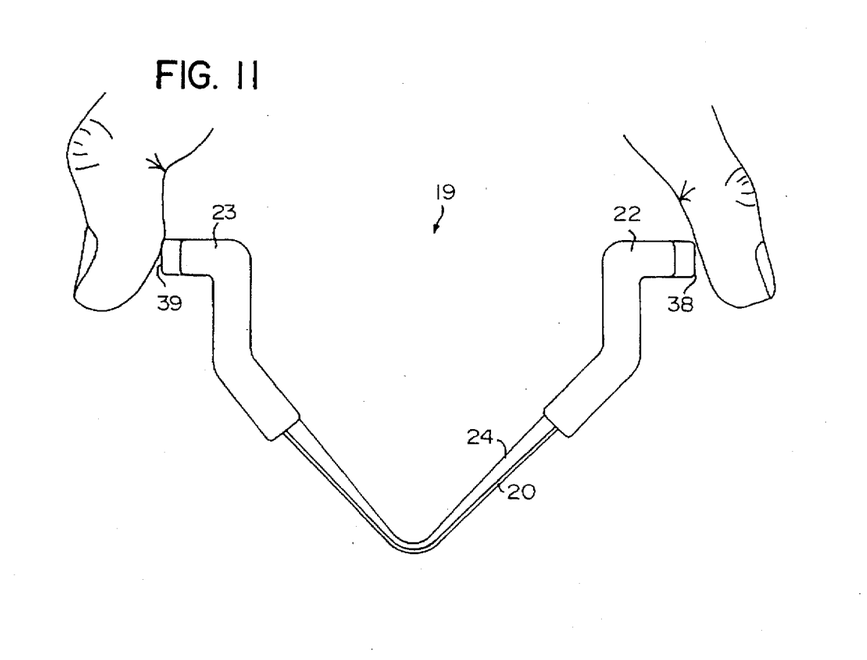
FIG. 11 is a front view of the flexible surgical razor of FIG. 10 in its flexed position as employed for the removal of organic skin tissue.

A fourth embodiment of the flexible surgical razor 19, in FIGS. 10 and 11, illustrates another alternative flexible sheath design. This embodiment is identical to the first embodiment, described above, except that the front and rear edges 46 and 47 of the flexible sheath 24 are designed with a concave shape, as illustrated in FIG. 10. This flexible sheath design will result in a flex as depicted in FIG. 11. The wider portions of the flexible sheath 24 will react less to inward finger pressure applied to the left and right exterior edges 38 and 39 of the left and right gripping extensions 22 and 23 than the narrower portions. This produces the sharp degree of curvature portrayed in FIG. 11.

Figure 12:
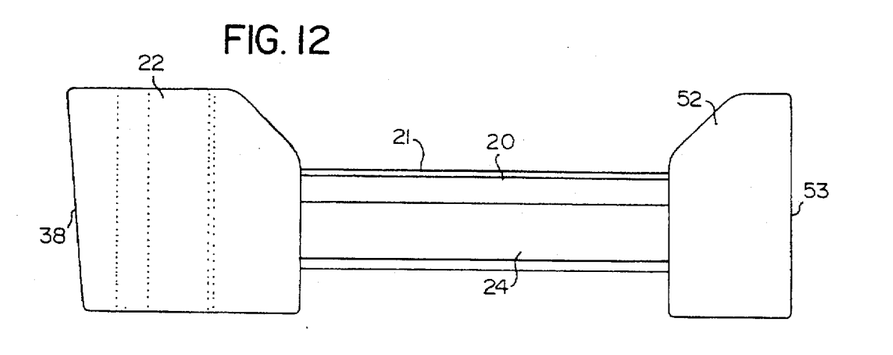
FIG. 12 is a top view of the flexible surgical razor of a fifth embodiment of the present invention.
Figure 13:
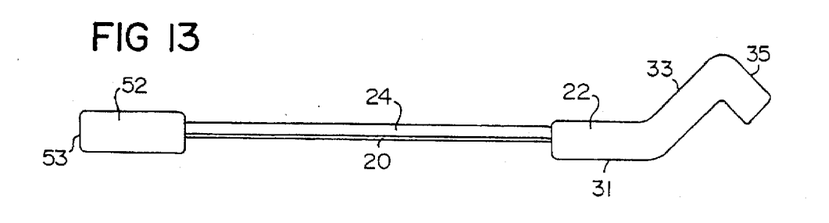
FIG. 13 is a front view of the flexible surgical razor of FIG. 12.

A fifth embodiment of the present invention only utilizes one specially designed gripping extension 22, as depicted in FIGS. 12 and 13. This embodiment is identical to the first embodiment, described above, except that only one of the gripping extensions 22 includes the inner 31, middle 33 and outer 35 segments, configured as described in the first embodiment. The other gripping extension only requires one segment 52, with an exterior gripping edge 53, attached to the other side edge of the flexible blade 20.

A sixth embodiment of the invention is described in FIGS. 14–20, which includes at least a row of a plurality teeth 60, 62 extending from the exterior gripping edges 38', 39' of the outer segment 35',36'. This embodiment is essentially identical to the embodiments of FIGS. 1–5 and FIG. 6–7, except the row or rows of the plurality of teeth provide the user's fingers full and complete control of the flexing of the flexible blade 20'.

Figure 14:
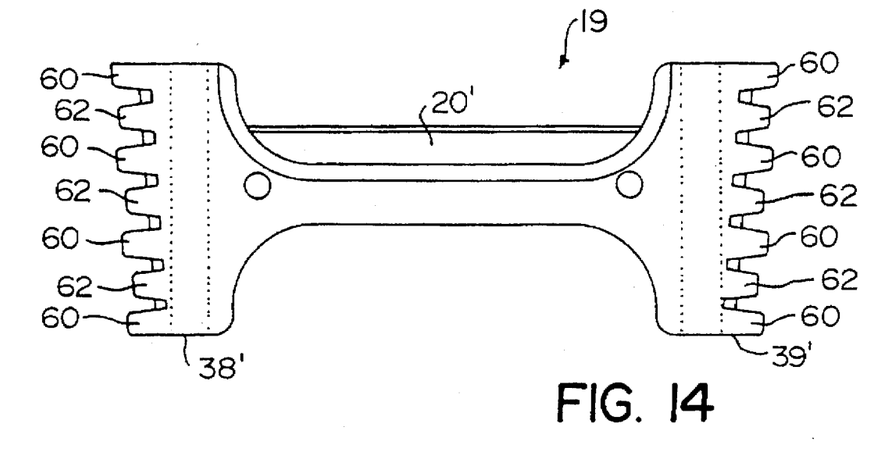
FIG. 14 is a top view of a sixth embodiment of the present invention.
Figure 15:
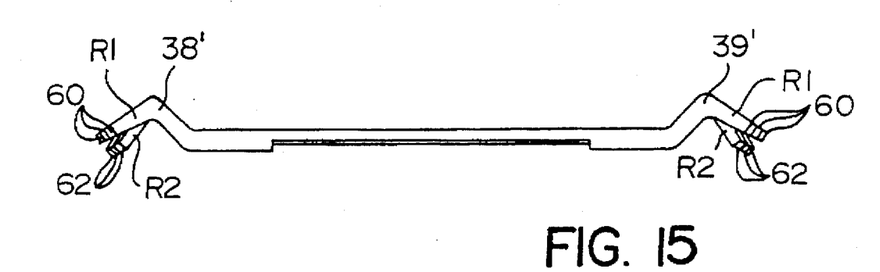
FIG. 15 is a side view of the flexible surgical razor of FIG. 14.
Figure 16:
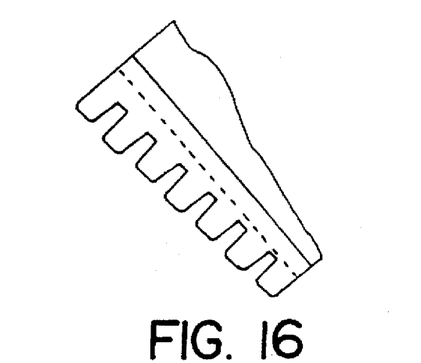
FIG. 16 is a partial auxiliary view of the flexible surgical razor of FIG. 14 in the direction of the arrow labeled "Auxiliary View."
Figure 17:
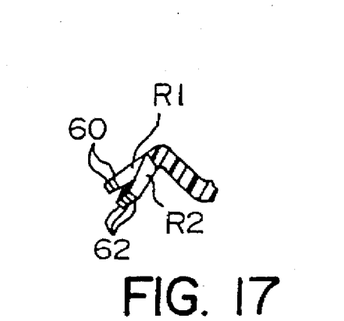
FIG. 17 is an sectional view taken along line B—B of FIG. 14.

As shown in FIGS. 14 and 15, a plurality of teeth 60,62 extend from the exterior gripping edges 38', 39'. The first row of teeth R1 includes three spaced apart teeth 60, with the second row of teeth R2 having three spaced apart teeth 62. As illustrated in FIG. 16 and 17, the first and second rows R1, R2 of the spaced apart teeth 60, 62 are asymmetrically angled to the intersection of the middle segment. As shown in FIG. 14 and 16, the first and second row R1, R2 of the teeth 60, 62 have the spacing between the teeth 60, 62 greater that the width of the teeth 60, 62. As illustrated, the second row R2 of teeth 62 is preferably positioned within the spaces between the first row R1 of the teeth 60 when the flexible razor is viewed from a top view. Also, the exterior edges of said the pair of gripping extensions are tapered along each row R1, R2 of teeth 60, 62 at an inward angle of about 5° toward the rear edge of said flexible blade.

Preferably, in this embodiment, the middle segment is angled about 45° to the plane of said razor blade, the outer segment has the first row R1 of teeth 60 is angled about 35° to the plane of the flexible razor blade, and the second row R2 of teeth 62 is angled about 65° to the plane of the flexible razor blade. Each of the teeth include an end surface defining a finger engagable surface controllable by the user, e.g., a truncated geometric figure having edges such as pyramid, cone or the like.

Figure 18:
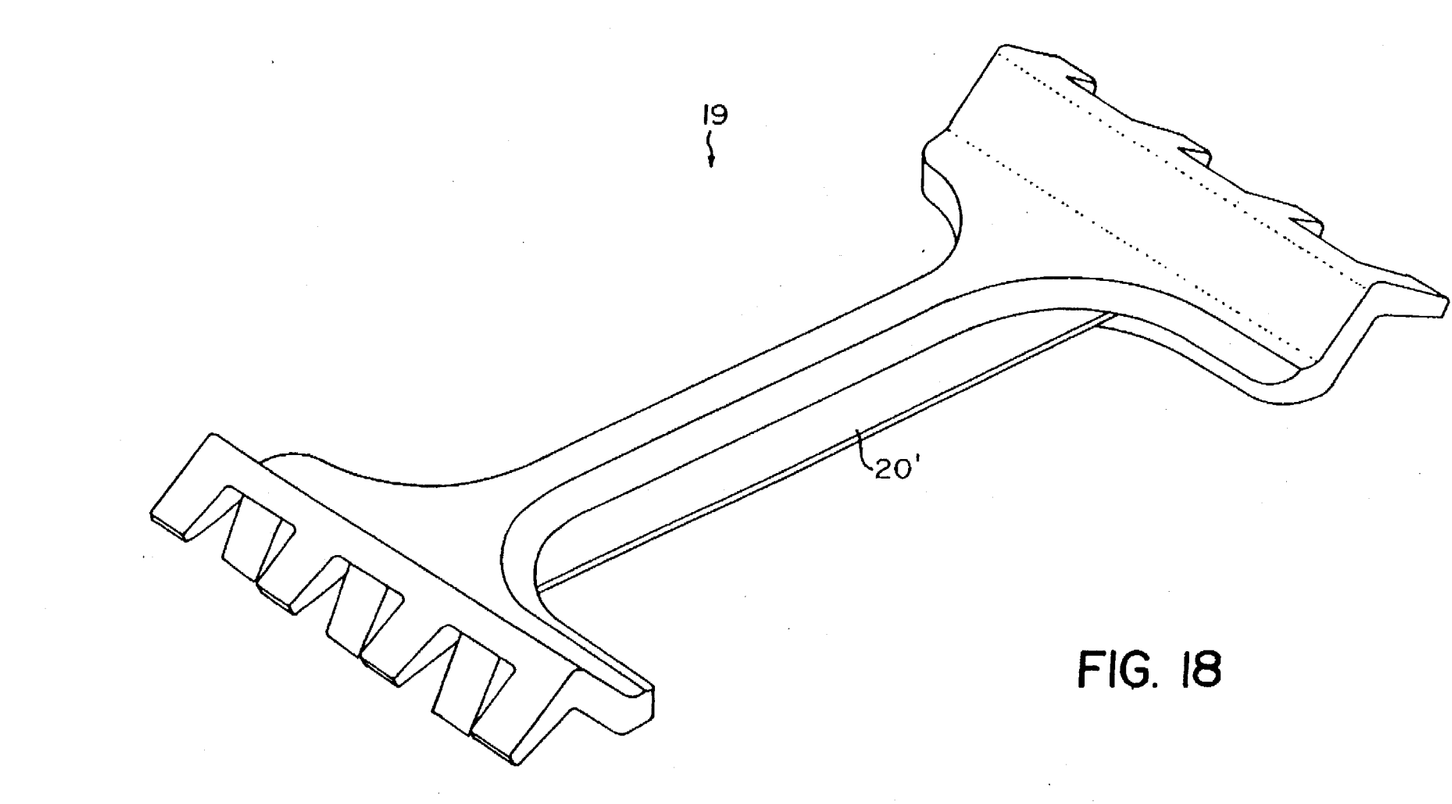
FIG. 18 is a perspective view of the flexible surgical razor of FIG. 14 in an unflexed posture.
Figure 19:
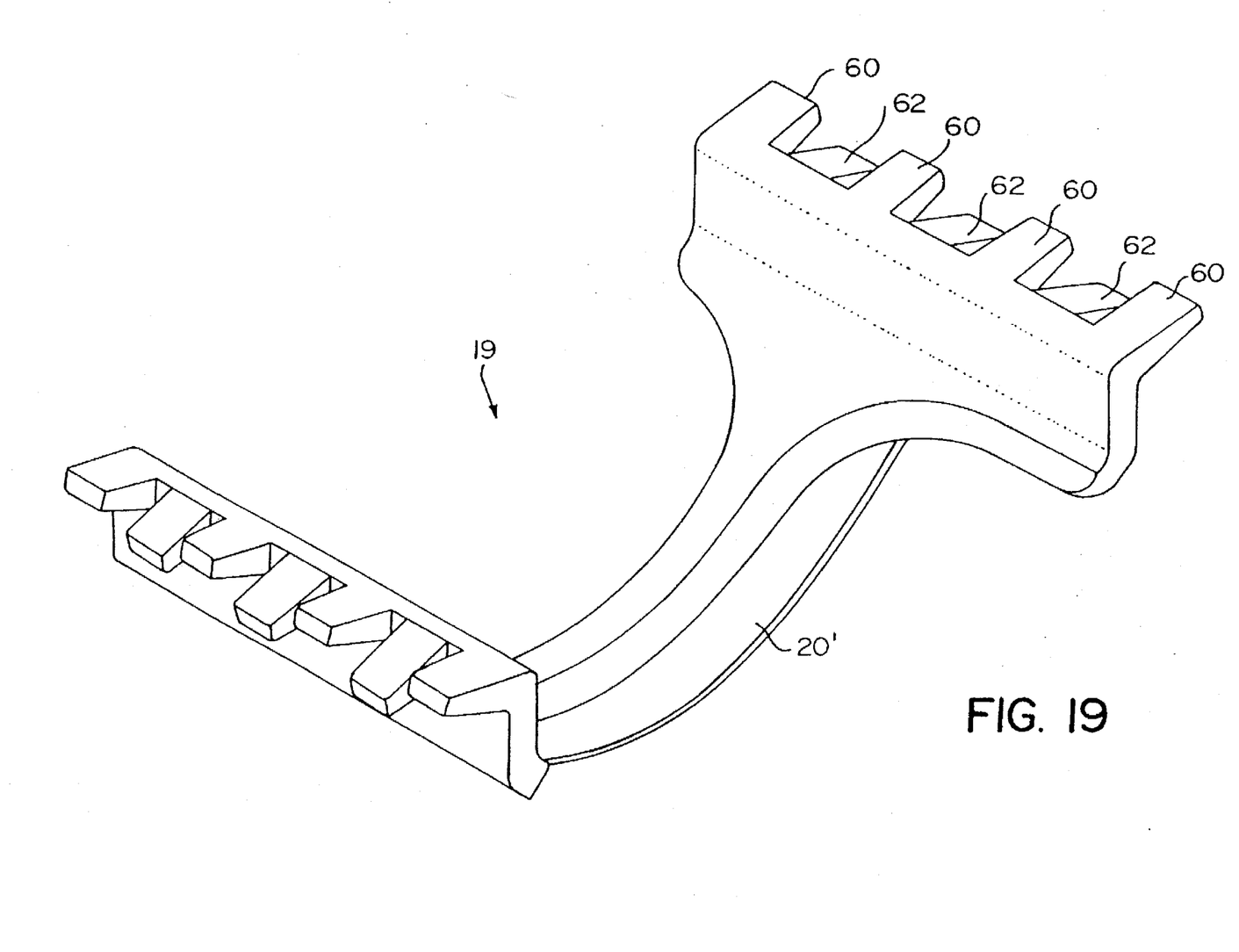
FIG. 19 is a perspective view of the flexible surgical razor of FIG. 14 in an initial flexed position illustrating the positioning of the first and second rows of teeth for finger engagement.
Figure 20:
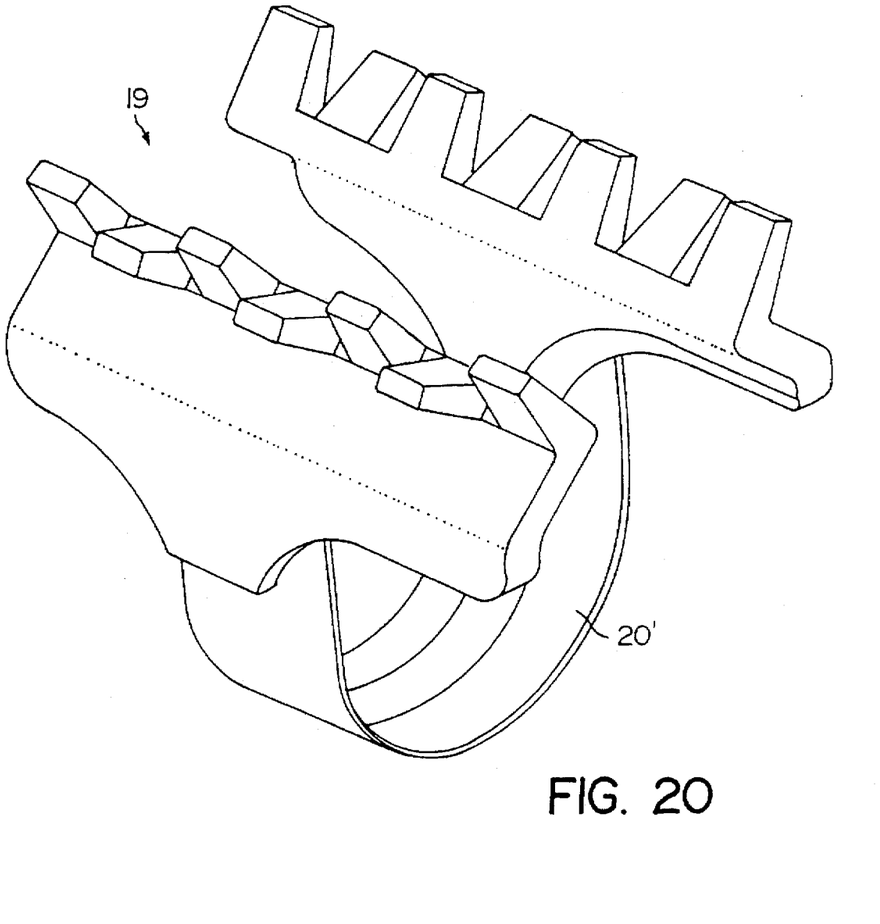
FIG. 20 is a perspective view of the flexible surgical razor of FIG. 14 in a fully flexed position illustrating the positioning of the first and second rows of teeth for finger engagement.

As illustrated in FIG. 18, the flexible blade 20' can be flexed by primarily engaging the upper row R1 of the teeth 60. As shown in FIG. 19, the flexible blade 20' is flexed by finger pressure to an initial flex position causing the lower row R2 of teeth 62 to be essentially rotated into a finger engagement position upon application of the pressure to the gripping extension. Thus, the finger engagement of the second row R2 of a plurality of spaced apart teeth 62 occurs upon flexing of said razor blade. As shown in FIG. 20, the lower row of teeth R2 becomes the primary engaging surface for the user's fingers as the flexible blade 20' is positioned in a full flex position. In this manner, full and complete control of the flexing is achieved, either by the user's thumb and index finger, or thumb and the first two finger digits engaging the ends of the row or rows R1, R2 of teeth 60, 62.

The embodiments described above provide for some significant improvements and advantages. A first advantage lies in the design of the left and right gripping extensions 22 and 23. As described above, the gripping extensions 22 and 23 regulate the direction of the flexible blade's curvature and improve the user's control over the extent of that curvature. Moreover, the design of the flexible sheath 24 facilitates further control over the extent of the flexible blade's curvature and regulates the flexible blade's shape. The third and fourth embodiments, described in detail above, depict the flexible sheath's effect on blade curvature, demonstrating the expanded versatility of this flexible surgical razor. The fifth embodiment illustrates that one gripping extension may be used to achieve suitable flexing. Finally, the sixth embodiment illustrates the use of first and/or second row(s) R1, R2 of the spaced apart teeth 60, 62 asymmetrically angled to the intersection of the middle segment in order to provide the user full and complete control the flexing of the flexible blade.

Of course, it should be understood that a wide range of changes and modifications can be made to the preferred embodiment described above. It is therefore intended that the foregoing detailed description be regarded as illustrative rather than limiting, and that it be understood that it is the following claims, including all equivalents, which are intended to define the scope of the invention.

We claim:

1. A razor comprising:
    a flexible blade having a front edge, left and right side edges, and a rear edge; and
    a pair of mirror image gripping extensions each having an inner segment attached to a side edge of said blade, an at least partially planar middle segment extending at an upward angle away from the blade, and an outer segment having an exterior gripping edge and extending at an intersecting angle with said middle segment, said gripping edge including a first row of a plurality of spaced apart teeth for finger engagement, said flexible blade flexing upon application of finger pressure to said gripping extensions.

2. The razor of claim 1, wherein said gripping edge further comprises a second row of a plurality of spaced apart teeth, said first and second rows of said spaced apart teeth asymmetrically angled to said middle segment.

3. The razor of claim 1 wherein said pair of gripping extensions further comprise a front edge running parallel to the front edge of the blade, and a rear edge running parallel to the rear edge of the blade.

4. The razor of claim 1 wherein a flexible sheath is integrally connected to said pair of gripping extensions, said sheath controlling the flexing of said flexible blade in response to finger pressure applied to said gripping extensions.

5. The razor of claim 1 wherein said teeth include an end having a finger engagable surface.

6. The razor of claim 1 wherein said middle segment is angled about 45° to the plane of said razor blade.

7. A razor comprising:
    a flexible blade having a front edge, left, and right side edges, and a rear edge; and
    a pair of mirror image gripping extensions each having an inner segment attached to a side edge of said blade, a middle segment extending at an upward angle of approximately 45° away from said flexible blade, and an outer segment having an exterior gripping edge and extending at an intersecting angle with said middle segment, said gripping edge including a first row of a plurality of spaced apart teeth for finger engagement, said first row of teeth being angled about 35° to said flexible blade, and said flexible blade flexing upon application of finger pressure to said gripping extensions.

8. A razor comprising:

a flexible blade having a front edge, left and right side edges, and a rear edge; and a pair of mirror image gripping extensions each having an inner segment attached to a side edge of said blade, a middle segment extending at an upward angle away from said flexible blade, and an outer segment having an exterior gripping edge and extending at an intersecting angle with said middle segment, said gripping edge including a first row of a plurality of spaced apart teeth for finger engagement, said teeth being tapered at an inward angle toward the rear edge of said flexible blade, and said flexible blade flexing upon application of finger pressure to said gripping extensions.

9. The razor of claim 7, wherein said inward angle is about 5°.

10. A razor comprising:

a flexible blade having a front edge, left and right side edges, and a rear edge; and a pair of mirror image gripping extensions each having an inner segment attached to a side edge of said blade, a middle segment extending at an upward angle away from said flexible blade, and an outer segment having an exterior gripping edge and extending at an intersecting angle with said middle segment, said gripping edge including a first row of a plurality of spaced apart teeth each including an end having a surface for finger engagement, and the spacing between at least two teeth being greater than the width of a single tooth, and said flexible blade flexing upon application of finger pressure to said gripping extensions.

11. A razor comprising:

a flexible blade having a keen front edge, left and right side edges, and a rear edge; and a pair of gripping extensions each having an inner segment attached to a side edge of said blade, an at least partially planar middle segment extending at an upward angle away from the blade, and an outer segment having an exterior gripping edge and extending at an intersecting angle with said middle segment, said gripping edge including a first and second row of a plurality of spaced apart teeth for finger engagement, said first and second rows of said spaced apart teeth asymmetrically angled to said middle segment, said flexible blade flexing upon application of pressure by finger engagement of said gripping extension.

12. The razor of claim 11, wherein said finger engagement of said second row of a plurality of spaced apart teeth occurs upon flexing of said razor blade.

13. The razor of claim 11 wherein said pair of gripping extensions further comprise a front edge running parallel to the front edge of the blade, and a rear edge running parallel to the rear edge of the blade.

14. The razor of claim 13 wherein a flexible sheath is integrally connected to said pair of gripping extensions, said sheath controlling the flexing of said flexible blade in response to finger pressure applied to said gripping extensions.

15. The razor of claim 11 wherein said teeth include an end having a finger engagable surface.

16. A razor comprising:

a flexible blade having a keen front edge, left and right side edges, and a rear edge; and a pair of gripping extensions each having an inner segment attached to a side edge of said blade, a middle segment extending at an upward angle of approximately 45° away from said flexible blade, and an outer segment having an exterior gripping edge and extending at an intersecting angle with said middle segment, said gripping edge including a first and second row of a plurality of spaced apart teeth for finger engagement, said first and second rows of said spaced apart teeth being asymmetrically angled to said middle segment with said first row of teeth being angled about 35° to said flexible blade and said second row of teeth being angled about 65° to said flexible blade, and said flexible blade flexing upon application of pressure by finger engagement of said gripping extension.

17. A razor comprising:

a flexible blade having a keen front edge, left and right side edges, and a rear edge; and a pair of gripping extensions each having an inner segment attached to a side edge of said blade, a middle segment extending at an upward angle away from said flexible blade, and an outer segment having an exterior gripping edge and extending at an intersecting angle with said middle segment, said gripping edge including a first and second row of a plurality of spaced apart teeth for finger engagement, said first and second rows of said spaced apart teeth being asymmetrically angled to said middle segment, and each of said first and second rows of teeth having the spacing between at least two teeth in the same row greater that the width of a single tooth, and said flexible blade flexing upon application of pressure by finger engagement of said gripping extension.

18. A razor comprising:

a flexible blade having a keen front edge, left and right side edges, and a rear edge; and a pair of gripping extensions each having an inner segment attached to a side edge of said blade, a middle segment extending at an upward angle away from said flexible blade, and an outer segment having an exterior gripping edge and extending at an intersecting angle with said middle segment, said gripping edge including a first and second row of a plurality of spaced apart teeth for finger engagement, said first and second rows of said spaced apart teeth being asymmetrically angled to said middle segment, and said exterior edges of said pair of gripping extensions being tapered at an inward angle toward the rear edge of said flexible blade, and said flexible blade flexing upon application of pressure by finger engagement of said gripping extension.

19. The razor of claim 18, wherein said inward angle is about 5°.

20. A razor comprising:

a flexible blade having a front edge, left and right side edges, and a rear edge;

one gripping extension having an inner segment attached to a side edge of said blade, an at least partially planar middle segment extending at an upward angle away from the blade, and an outer segment having an exterior gripping edge and extending at an intersecting angle with said middle segment, said gripping edge including a first and second row of a plurality of spaced apart teeth for finger engagement, said first and second rows of said spaced apart teeth asymmetrically angled to said middle segment, said flexible blade flexing upon application of pressure by finger engagement of said gripping extension; and a second gripping extension attached to the other side edge of said flexible blade and having an exterior gripping edge.

21. A razor comprising:

a flexible blade having a front edge, left and right side edges, and a rear edge;

one gripping extension having an inner segment attached to a side edge of said blade, a middle segment extending at an upward angle away from said flexible blade, and an outer segment having an exterior gripping edge and extending at an intersecting angle with said middle segment, said gripping edge including a first and second row of a plurality of spaced apart teeth for finger engagement, said first and second rows of said spaced apart teeth asymmetrically angled to said middle segment, said exterior edges of said pair of gripping extensions being tapered at an inward angle toward the rear edge of said flexible blade, and said flexible blade flexing upon application of pressure by finger engagement of said gripping extension; and a second gripping extension attached to the other side edge of said flexible blade and having an exterior gripping edge.

22. The razor of claim 21, wherein said inward angle is about 5°.

23. A razor comprising:

a flexible blade having a front edge, left and right side edges, and a rear edge;

one gripping extension having an inner segment attached to a side edge of said blade, a middle segment extending at an upward angle of approximately 45° away from said flexible blade, and an outer segment having an exterior gripping edge and extending at an intersecting angle with said middle segment, said gripping edge including a first and second row of a plurality of spaced apart teeth for finger engagement, said first and second rows of said spaced apart teeth asymmetrically angled to said middle segment with said first row of teeth being angled about 35° to said flexible blade and said second row of teeth being angled about 65° to said flexible blade, and said flexible blade flexing upon application of pressure by finger engagement of said gripping extension; and a second gripping extension attached to the other side edge of said flexible blade and having an exterior gripping edge.

* * * * *